US006183696B1

(12) United States Patent
Elkind et al.

(10) Patent No.: US 6,183,696 B1
(45) Date of Patent: Feb. 6, 2001

(54) OPTICALLY BASED MINIATURIZED SENSOR WITH INTEGRATED FLUIDICS

(75) Inventors: Jerry Elkind, Richardson; Richard A. Carr, Rowlett; Jose Melendez, Plano, all of TX (US)

(73) Assignee: Texas Instruments Incorporated, Dallas, TX (US)

(*) Notice: Under 35 U.S.C. 154(b), the term of this patent shall be extended for 0 days.

(21) Appl. No.: 09/009,990

(22) Filed: Jan. 21, 1998

Related U.S. Application Data

(60) Provisional application No. 60/036,150, filed on Jan. 22, 1997, now abandoned.

(51) Int. Cl.[7] .................................................. G01N 21/17
(52) U.S. Cl. ..................... 422/82.05; 356/445; 436/164
(58) Field of Search ............................ 422/82.06, 82.07, 422/82.05; 356/445, 318, 317, 345, 446; 436/139–42, 144, 164, 165, 170, 171, 113, 121, 131

(56) References Cited

U.S. PATENT DOCUMENTS 5,545,567 * 8/1996 Gretillat et al. .
5,898,503 * 4/1999 Keller et al. .
5,946,083 * 8/1999 Melendez et al. .

* cited by examiner

Primary Examiner—Timothy M. Speer
Assistant Examiner—Jennifer McNeil
(74) Attorney, Agent, or Firm—W. Daniel Swayze, Jr.; Wade James Brady, III; Frederick J. Telecky, Jr.

(57) ABSTRACT

A miniaturized sensor (100) that improves the confidence measure of a given sample reading by directing the flow of sample to the sensor/sample interface (117) and thus bringing the sample reliably in contact with the sensor's biosensing film. An inlet flow channel (105) extending from the bottom (125) of the sensor (100) to the sensing surface (120). The inlet channel (105) guides the sample to a cavity 115 formed at a housing surface (120) where it interacts with the film deposit (117). An outlet channel (110) extends from the cavity (115) to the bottom surface (125) and directs the sample outside the device. The light source (58), detector array (68) and interface (54) can be added to the structure providing a fully integrated miniaturized sensor. Various well known methods of manufacturing may be used including mill casting, split molding and double mold processes.

18 Claims, 3 Drawing Sheets

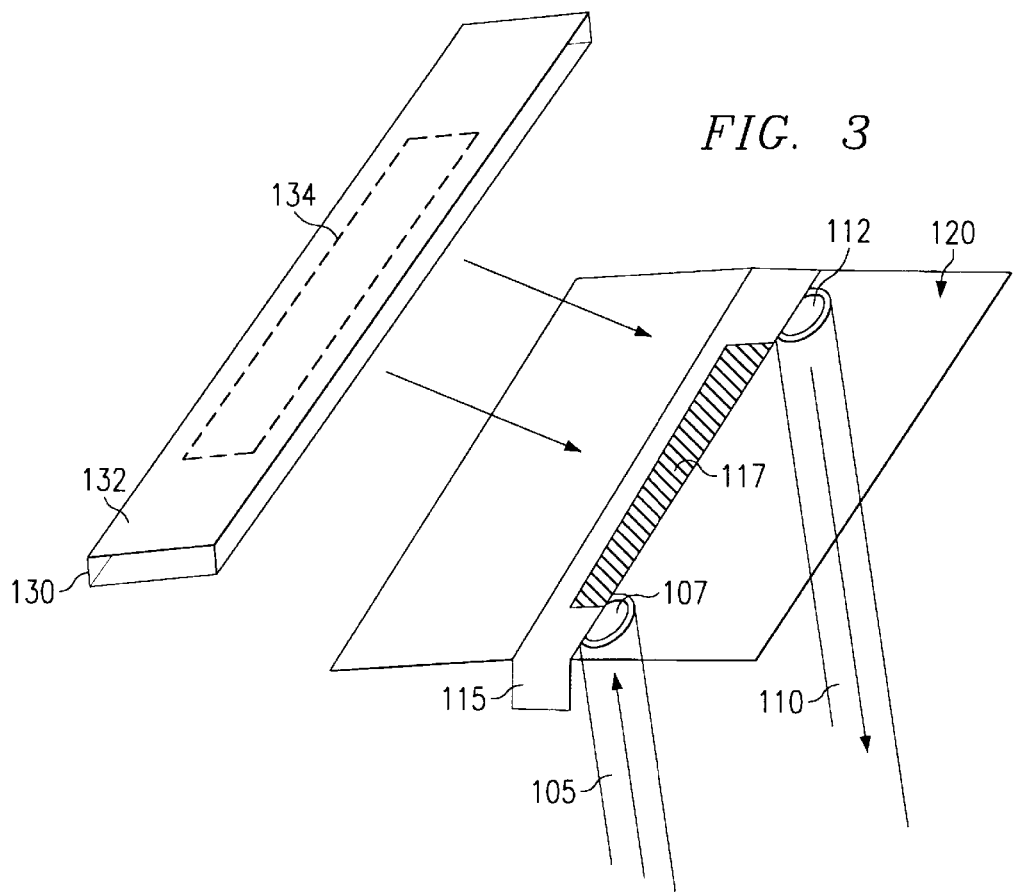
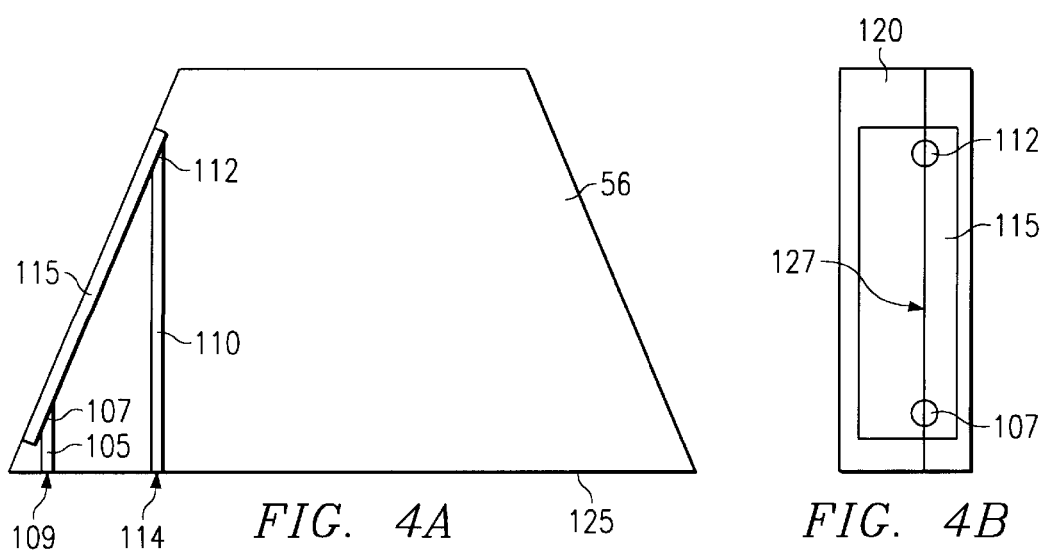

OPTICALLY BASED MINIATURIZED SENSOR WITH INTEGRATED FLUIDICS

This application claims priority under 35 USC § 119(e)(1) of provisional application Ser. No. 60/036,150 filed Jan. 22, 1997, abandoned.

TECHNICAL FIELD

The present invention relates in general to the field of optic based sensors and more specifically to a miniaturized sensor platform with integrated flow channels for directing the sample analyte of interest uniformly over the sensor/sample interface.

BACKGROUND OF THE INVENTION

Without limiting the scope of the invention, its background is described in connection with the Surface Plasmon Resonance ("SPR") phenomenon in connection with miniaturized optical sensors. It should be understood that the principles disclosed may be applied to various sensor configurations including light transmissive, fluorescence-based and critical angle among others.

Optical sensor systems have been developed and used in the fields of chemical, biochemical, biological or biomedical analysis, process control, pollution detection and control and other areas. With SPR-based optical sensors, a resonance is observed when a polarized beam of monochromatic light is totally internally reflected from a dielectric surface having a thin metal film formed thereon. The light internally reflected at the surface has a minimum intensity at a particular angle referred to as the resonant angle. This angle is determined by the dielectric conditions adjacent the metal film and the properties of the film itself. The interface between the sensor surface and the sample of interest shall be referred to as the "sensor/sample interface."

Recent advances in light emitting components and detectors units have allowed the design of small, lightweight, fully integrated sensors. Such sensors can measure less than a few centimeters in length and are easily transported and used near the sample of interest. In addition, since most of the sensor components are readily available their overall cost of manufacturing is low.

While miniaturized sensors are becoming available for use in a wide range of field applications, their effectiveness as an analytical tool is largely determined by the properties of the sample analyte of interest. Fluctuations in sample concentration, temperature and other environmental conditions effect the reactive properties of film deposit in the presence of the sample. Ideally, a controlled amount of the sample with uniform properties is brought in contact with the sensor/sample interface during the sampling process. With larger systems, a flow cell may be used to control the flow rate of the sample. However, there is no equivalent control mechanism for the miniaturized optical sensors.

Accordingly, a device configuration that channels a uniform quantity of the sample analyte of interest across the reactive film deposit of sensor's sampling surface would ensure a more confident analysis.

SUMMARY OF THE INVENTION

The present invention discloses a miniaturized sensor platform with integrated channels for controlling the flow of sample over the sensor/sample interface.

A primary object of the present invention is to provide a miniaturized integrated sensor capable of use in optically guided sensing applications. The sensor package of the present invention integrates a light source, detector means, light guide optics and a simplified system interface into a compact miniaturized package. Flow channels are molded inside the sensor housing and extend to an area along the sensor sampling surface. In one embodiment, an inlet channel guides the sample into the housing from the outside where it collects in a cavity topped by a portion of the biosensing film. A constant flow of pressure is provided to move the sample via an outlet channel to the outside.

Another object of the present invention is to provide a biosensor configuration that can be inserted into a hand held instrument for practical field use. The instrument provides an opening where the sample to be tested is poured, collected and directed towards the sensor. Function buttons control the instrument's operation and a display may be provided for on-the-spot analysis. This may be particularly advantageous where a preliminary diagnosis of sample properties is required prior to more thorough analysis at a larger facility. In this regard, the instrument can be equipped with a storage compartment or the sample poured into a container for transport.

Disclosed in one embodiment of the invention, is a miniaturized sensor package that improves the confidence measure of given sample reading by directing the flow of sample uniformly over the biosensing film of the sensor. An inlet channel is provided with an opening at a sensor surface that guides the sample to a cavity carved out along the sampling surface interface. An outlet channel directs the sample of interest outside the device. The light source, detector array and interface form part of the sensor providing a fully integrated device. Various well known methods of manufacturing may be used including mill casting, split molding and double mold processes.

For a more complete understanding of the present invention, including its features and advantages, reference is now made to the following detailed description, taken in conjunction with the accompanying drawings.

BRIEF DESCRIPTION OF THE DRAWINGS

In the drawings:

FIG. 3 shows an expanded view of the flow cavity and cavity cap used in one embodiment of the present invention;

FIGS. 4a and 4b depict two sides of a flow channel sensor according to one embodiment of the invention.

Corresponding numerals and symbols in the different figures refer to corresponding parts unless otherwise indicated.

DETAILED DESCRIPTION OF THE PREFERRED EMBODIMENT

Figure 1:
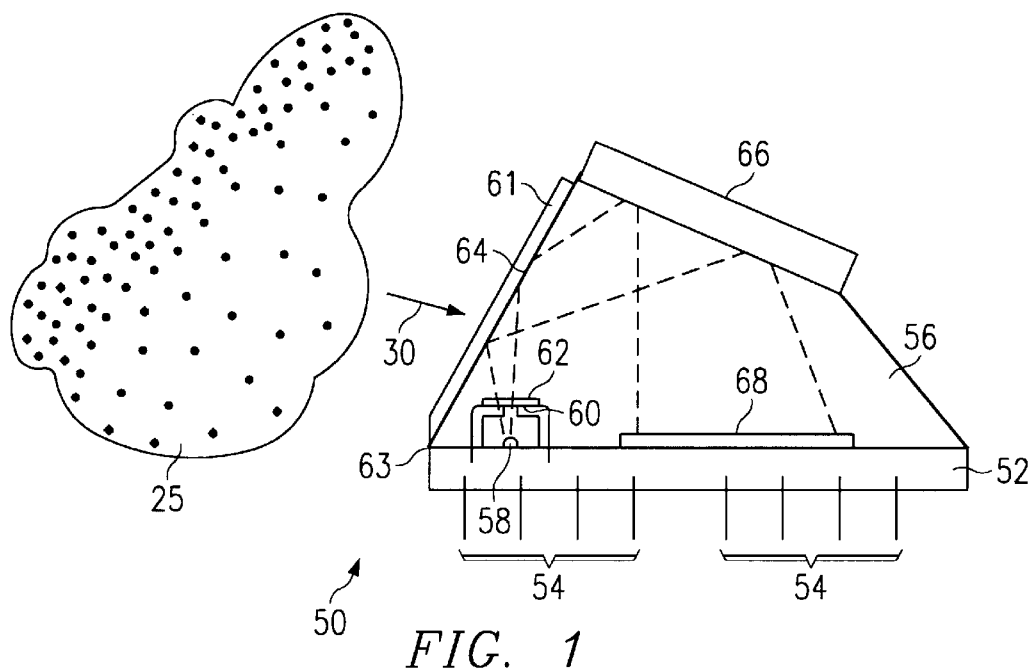
FIG. 1 depicts a prior art SPR miniaturized sensor package.

In FIG. 1 an integrally formed optically based Surface Plasmon Resonance ("SPR") sensor 50 is shown in close proximity to a sample 25 analyte of interest which can be a liquid or gas. The sample may be any (bio)chemical substance for which an indicator interaction is known and which can be formed into a thin biosensing layer 61. The film is deposited on a surface 63 of the sensor and exposed to the sample 25 during analysis. Various ways of bringing the sample 25 in contact with the surface 63 may be employed such as by dipping, dropping or by using a flow cell.

As shown, a substrate 52 forms a device platform to which a light transmissive housing 56 is coupled. The housing material can be plastic, glass or other similar optic coupling substance. A light source is preferably located above or within the substrate 52 and has an aperture 58 there over allowing light to pass. In one embodiment, the light source is a single high intensity light emitting diode. A polarizer 62 is located near the aperture 58 to polarize passing light which, in turn, continues through housing 56 and strikes a SPR layer 64 which is preferably formed on an exterior surface of the housing 56.

The SPR layer 64 may be deposited directly or placed on a glass slide or the like. This configuration achieves an optical surface phenomenon that can be observed when the polarized light is totally internally reflected from the interface between the layer 64 and the sample of interest. This principle is well understood by those skilled in the art and discussed by Ralph C. Jorgensen, Chuck Jung, Sinclair S. Yee, and Lloyd W. Burgess, in their article entitled *Multi-wavelength surface plasmon resonance as an optical sensor for characterizing the complex refractive indices of chemical samples*, Sensors and Actuators B, 13–14, pp. 721–722, 1993.

Analysis is permitted by using a mirrored surface 66 which directs the reflected light onto a detector array 68. The detector array 68, in turn, senses illumination intensity of the reflected light rays. For optical radiation, a suitable photodetector array 68 is the TSL213, TSL401, and TSL1401, with a linear array of resolution n×1 consisting of n discrete photo sensing areas, or pixels. In the detector array 68, light energy striking a pixel generates electron-hole pairs in the region under the pixel. The field generated by the bias on the pixel causes the electrons to collect in the element while the holes are swept into the substrate.

Each sensing area in the photodetector array 68 thereby produces a signal on an output with a voltage that is proportional to the intensity of the radiation striking the photodetector 68. This intensity and its corresponding voltage are at their maxima in the total internal reflection region. Electrical connections 54 are coupled to one end of the substrate 52 and provides a signal pathway from the detector 68 output to the external world.

FIG. 1 illustrates a sensing approach wherein the sample 25 is brought in contact 30 with the SPR layer 64 for analysis. This arrangement, however, may lead to unreliable results since analysis is influenced primarily by the properties of the sample 25. For instance, the sample concentration may vary throughout the sample mass or with time. Likewise, movement of the sensor 50 during analysis changes the orientation of layer 64 with respect to the sample 25. This is especially true in portable hand held applications where the sensor 50 is brought to the sample.

Figure 2:
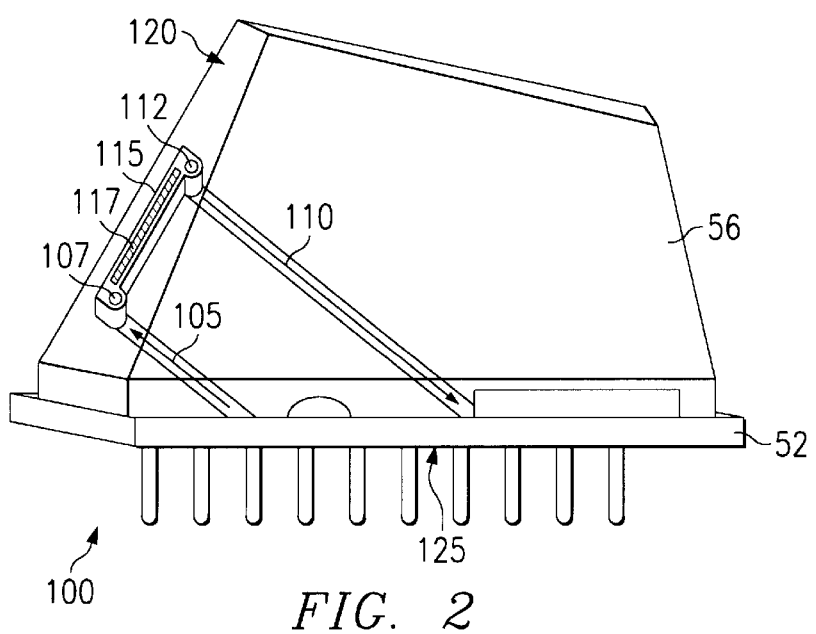
FIG. 2 is a perspective view of a flow channel sensor according to one embodiment of the invention.

Turning now to FIG. 2, an improved sensor configuration according to the invention is shown and denoted generally as 100. Sensor 100 is similar to sensor 50 in most respects, but differs primarily by the integrally formed flow channels 105 and 110 inside the housing structure 56. As shown, the channels 105, 110 extend inside the housing 56 from a first surface 120 to a second surface 125 and pierce the platform 52 to the outside. This permits the sample to flow inside the sensor housing 56 through channel 105 and enter the cavity 115 via the opening 107. The sample flows over the metal film 117 which is deposited by known means on the bottom surface of the cavity 115.

The process of directing the sample over the sensor/sample interface is illustrated in FIG. 3. According to one embodiment, the chemical reagent 117 is deposited at the bottom of the cavity 115 to form the sensor/sample interface. In this configuration, flow channel 105 acts as an inlet passageway inside the housing 56 and directs the sample (not shown) from the bottom surface 125 of the sensor 100 to the cavity 115. The sample collects inside the cavity 115 and flows over the sensor/sample interface 117 and is directed to opening 112 through channel 110 and outside the sensor 100. In this way, the sample is guided in contact with the sensor/sample interface 117.

FIG. 3 also shows a cavity cap 130 which completes the sample passageway formed by channels 105, 110 and cavity 115 by sealing the open area of the cavity 115. In one preferred embodiment, cap 130 is a band-aid like structure that covers the top of the cavity 115. A nonreactive material 134, such as a teflon, coats a portion of the cap that lies directly above the open cavity. The material 134 is surrounded by a metal layer 132 to complete the cap. In one embodiment, the metal layer 132 is a piece of aluminum tape, although other similar materials may be used.

Accordingly, the present invention provides a sensor configuration that reliably directs a sample over a sensors' sampling surface. It should be understood, however, that other miniaturized sensor configurations may benefit from the principles of the present invention. These include critical angle, light transmission and fluorescence-based sensors as well as others known to those skilled in the art.

While flow channels 105 and 110 are shown extending from bottom surface 125 to surface 120 according to one possible sensor configuration 100, it should be understood that other similar arrangements of the flow channels 105, 110 may be achieved without departing from the true scope and spirit of the invention. For example, the flow channels 105, 110 may extend from other surfaces of the sensor 100 such as surfaces 130 or 135. Also, multiple flow channel and cavity configurations may be employed. Other suitable configurations will be apparent to those skilled in the art upon reference to this disclosure and it is intended that such uses be covered by the invention.

Turning now to FIG. 4a, a side profile view of the housing 56 is shown. The flow channels 105, 110 extend from cavity 115 to bottom surface 125. Channel 105 has openings 107 and 109 at opposite ends which define a fluidic inlet passageway from outside the sensor 100 to cavity 115. Likewise, channel 110 has openings 112 and 114 which provide a fluidic passageway for transporting the sample from the cavity 115 to the outside world.

FIG. 4b shows a front view of the sensing surface 120 and cavity 115 with openings 107 and 112 slightly off center about line 127. Thus a major portion of the area defined by the cavity 115 is filled with the sample of interest which first enters the cavity 115 through opening 107 and exits the cavity 115 through opening 112.

Figure 5:
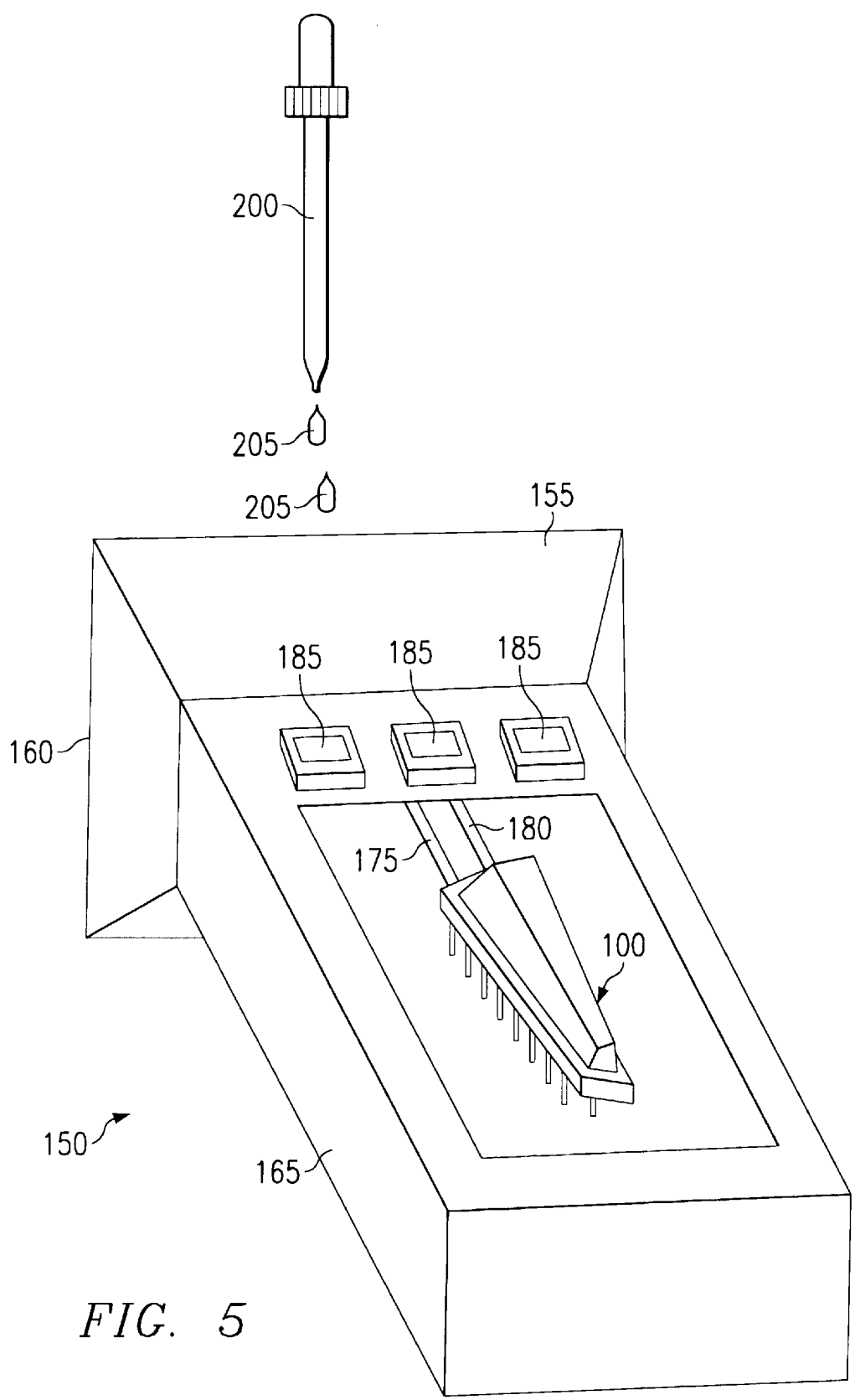
FIG. 5 shows use of a flow channel sensor in a hand held instrument application.

Turning now to FIG. 5, the improved sensor 100 is shown in use in a hand held instrument 150. A sample dispenser 200 is used to place the particular sample of interest 205 into a receptor 155 of the instrument 150. Other methods and means of introducing the sample 205 to the instrument 150 are contemplated.

In one embodiment, the receptor is open (not shown in this perspective) at end 160. This allows the sample to be gravity guided to the sensor 100. Alternatively, a pressure or vacuum means can be provided inside the instrument 150 to direct the sample to the sensor 100.

As shown, instrument 150 has a base 165 which houses the sensor 100 inside. In some contemplated applications, the sensor is removed and inserted into a fitted mount or socket inside the instrument 150. Passage 175 is utilized to bring the sample 205 to the sensor 100 while passage 180 removes it providing a flow of sample 205 for analysis. The flow of the sample 205 and other instrument functions may be controlled with keys 185.

In one contemplated use of the instrument 150, the sensor 100 is placed inside the instrument prior to use. The sample 205 is then introduced into the instrument 150 and analysis of the sensor is performed according to well known methods. After analysis, the sensor 100 can be removed, replaced or disposed.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An optically based miniaturized sensor for detecting properties of a given sample analyte comprising:
   a platform having a top and a bottom;
   a housing coupled to the top of said platform, said housing having at least first and second surfaces;
   a first flow channel extending from said bottom of said platform to said first surface of said housing;
   a second flow channel extending inside said housing adjacent said first flow channel;
   a cavity formed about said first surface of said housing and providing a passageway from said first flow channel to said second flow channel; and
   a cavity cap forming a seal over said cavity.

2. The optically based miniaturized sensor according to claim 1 further comprising:
   a set of electrical connections extending from said bottom of said platform;
   a light source coupled to said top of said platform and embedded in said housing, said light source arranged to emit light in the direction of said first surface; and
   a detector coupled to said platform arranged to receive light from said second surface, said detector operably coupled to said set of electrical connections.

3. The optically based miniaturized sensor according to claim 1 further comprising a thin layer of biosensing material covering a bottom portion of said cavity.

4. The sensor according to claim 1 wherein said cavity cap comprises a nonreactive inner portion and an outer tape portion.

5. The optically based miniaturized sensor according to claim 1 wherein the sensor has a fluorescence-based configuration.

6. The optically based miniaturized sensor according to claim 1 wherein the sensor has a light transmission configuration.

7. The optically based miniaturized sensor according to claim 1 wherein the sensor has a critical angle configuration.

8. The optically based miniaturized sensor according to claim 1 wherein said first flow channel and said second flow channel are substantially parallel.

9. An optically based miniaturized sensor for detecting properties of a given sample analyte comprising:
   a platform having a top and a bottom;
   a housing coupled to the top of said platform, said housing having at least first and second surfaces;
   a first flow channel extending from said bottom of said platform to said first surface of said housing;
   a second flow channel extending inside said housing adjacent said first flow channel;
   a cavity formed about said first surface of said housing and providing a passageway from said first flow channel to said second flow channel; and
   a thin layer of biosensing material covering a bottom portion of said cavity;
   wherein said thin layer of biosensing material is a surface plasmon resonance layer.

10. A hand held portable sensing instrument for detecting the presence of one or more sample analytes, said instrument comprising:
    a base forming an enclosure for housing a plurality of instrument components;
    a receptor coupled to said base and having an open end for receiving said sample analytes; and
    an optically based miniaturized sensor inside said enclosure and interfaced to said receptor via fluid passageways;
    wherein said sensor is a surface plasmon resonance sensor.

11. The hand held portable sensing instrument according to claim 10 further comprising a plurality of functions keys for controlling the flow of said sample analytes from said receptor to said sensor.

12. The hand held portable sensing instrument according to claim 10 wherein said sensor further comprises:
    a device platform having a top and a bottom;
    a housing coupled to top of said platform, said housing having at least first and second surfaces;
    an inlet flow channel extending from said bottom of said platform to said first surface inside said housing, said first flow channel having opening at one end coupled to at least one fluid passageway;
    an outlet flow channel extending inside housing adjacent said inlet flow channel and having an opening at one end coupled to a second fluid passageway; and
    a cavity forming an opening about said first surface of said housing and joining said first openings of said first and second flow channels.

13. A hand held portable sensing instrument for detecting the presence of one or more sample analytes, said instrument comprising:
    a base forming an enclosure for housing a plurality of instrument components;
    a receptor coupled to said base and having an open end for receiving said sample analytes; and
    an optically based miniaturized sensor inside said enclosure and interfaced to said receptor via fluid passageways;
    wherein said optically based miniaturized sensor further comprises:
    a device platform having a top and a bottom;
    a housing coupled to top of said device platform, said housing having at least first and second surfaces;
    an inlet flow channel extending from said bottom of said device platform to said first surface inside said housing, said first flow channel having a first opening at one end coupled to at least one fluid passageway;
    an outlet flow channel extending inside said housing adjacent said inlet flow channel and having a second opening at one end coupled to a second fluid passageway;

a cavity forming an opening about said first surface of said housing and joining said first and second openings of said first and second flow channels; and a cap covering an open area of said cavity.

14. A miniaturized biosensor for detecting properties of a given sample of interest comprising:

a platform having a top and a bottom;

a set of electrical connections extending from said bottom of said platform;

a light transmissive housing having a first surface with a cavity formed thereon and a second surface, said housing coupled to the top of said platform;

a light source coupled to said top of said platform inside said light transmissive housing, said light source arranged to emit light in the direction of said first surface;

a detector coupled to said platform adjacent said light source and arranged to receive light from said second surface of said light transmissive housing, said detector operably coupled to said set of electrical connections;

a first flow channel extending inside said light transmissive housing from an opening on said platform to said first surface of said light transmissive housing;

a second flow channel extending adjacent to said first flow channel inside said light transmissive housing; and a thin film of biosensing material covering a bottom portion of said cavity;

wherein said cavity forms a passageway from said first flow channel to said second flow channel; and a cavity cap forming a seal over said cavity.

15. The sensor according to claim 14 wherein said cavity cap comprises a nonreactive inner portion and an outer tape portion.

16. The sensor according to claim 15 wherein said nonreactive inner portion is made of a teflon material and said outer tape portion is made of an aluminum.

17. A miniaturized biosensor for detecting properties of a given sample of interest comprising:

a platform having a top and a bottom;

a set of electrical connections extending from said bottom of said platform;

a light transmissive housing having a first surface with a cavity formed thereon and a second surface, said light transmissive housing coupled to the top of said platform;

a light source coupled to said top of said platform inside said light transmissive housing, said light source arranged to emit light in the direction of said first surface;

a detector coupled to said platform adjacent said light source and arranged to receive light from said second surface of said light transmissive housing, said detector operably coupled to said set of electrical connections;

a first flow channel extending inside said light transmissive housing from an opening on said platform to said first surface of said light transmissive housing;

a second flow channel extending adjacent to said first flow channel inside said light transmissive housing; and a thin film of biosensing material covering a bottom portion of said cavity;

wherein said thin film is a surface plasmon resonance layer.

18. The sensor according to claim 17 wherein said first flow channel is substantially parallel to said second flow channel.

* * * * *